US00PP20351P2

(12) United States Plant Patent
Kobayashi

(10) Patent No.: US PP20,351 P2
(45) Date of Patent: Sep. 22, 2009

(54) POINSETTIA PLANT NAMED 'PER10606'

(50) Latin Name: *Euphorbia pulcherrima*
Varietal Denomination: PER10606

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 12/152,684

(22) Filed: May 14, 2008

(51) Int. Cl.
*A01H 5/00* (2006.01)

(52) U.S. Cl. ..... Plt./304

(58) Field of Classification Search ..... Plt./304
See application file for complete search history.

*Primary Examiner*—June Hwu
(74) *Attorney, Agent, or Firm*—C. A. Whealy

(57) ABSTRACT

A new and distinct cultivar of Poinsettia plant named 'PER10606', characterized by its uniform, upright and mounded plant habit; moderately vigorous growth habit; freely branching habit; dark green-colored leaves; early season flowering response; inflorescences with creamy white-colored flower bracts; and excellent post-production longevity.

1 Drawing Sheet

Botanical designation: *Euphorbia pulcherrima.*
Cultivar denomination: 'PER10606'.

BACKGROUND OF THE INVENTION

The present invention relates to a new and distinct cultivar of Poinsettia plant, botanically known as *Euphorbia pulcherrima* Willd., and hereinafter referred to by the name 'PER10606'.

The new Poinsettia is a naturally-occurring whole plant mutation of *Euphorbia pulcherrima* Willd. '7-05', not patented. The new Poinsettia was discovered and selected by the Inventor as a single plant within a population of plants '7-05' in a controlled greenhouse environment in Encinitas, Calif. on Dec. 2, 2005.

Asexual reproduction of the new Poinsettia by terminal vegetative cuttings in a controlled greenhouse environment in Encinitas, Calif. since February, 2006, has shown that the unique features of this new Poinsettia are stable and reproduced true to type in successive generations of asexual reproduction.

SUMMARY OF THE INVENTION

The new Poinsettia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER10606'. These characteristics in combination distinguish 'PER10606' as a new and distinct cultivar of Poinsettia:

1. Uniform, upright and mounded plant habit.
2. Moderately vigorous growth habit.
3. Freely branching habit.
4. Dark green-colored leaves.

5. Early season flowering response; under natural season conditions, plants flower in about seven weeks in Encinitas, Calif.
6. Inflorescences with creamy white-colored flower bracts.
7. Excellent post-production longevity.

In side-by-side comparisons conducted in Encinitas, Calif. plants of the new Poinsettia differed from plants of the parent, '7-05', primarily in flower bract color as plants of '7-05' have light pink and creamy white bi-colored flower bracts.

Plants of the new Poinsettia can be compared to plants of the *Euphorbia pulcherrima* Willd. 'Peterstar White', disclosed in U.S. Plant Pat. No. 9,878. In side-by-side comparisons conducted in Encinitas, Calif., plants of the new Poinsettia differed from plants of 'Peterstar White' in the following characteristics:

1. Plants of the new Poinsettia had darker green-colored leaves than plants of 'Peterstar White'.
2. Plants of the new Poinsettia flowered about three weeks earlier than plants of 'Peterstar White' under natural season conditions.
3. Plants of the new Poinsettia and 'Peterstar White' differed slightly in flower bract color.

Plants of the new Poinsettia can be compared to plants of the *Euphorbia pulcherrima* Willd. '490 White', disclosed in U.S. Plant Pat. No. 8,772. In side-by-side comparisons conducted in Encinitas, Calif., plants of the new Poinsettia differed primarily from plants of '490 White' in time to flower as plants of the new Poinsettia flowered about eleven days earlier than plants of '490 White' under natural season conditions.

BRIEF DESCRIPTION OF THE PHOTOGRAPHS

The accompanying photographs illustrate the overall appearance of the new Poinsettia. These photographs show the colors as true as it is reasonably possible to obtain in colored reproductions of this type. Colors in the photographs may differ slightly from the color values cited in the detailed botanical description which accurately describe the colors of the new Poinsettia.

The photograph at the bottom of sheet comprises a side perspective view of a typical flowering plant of 'PER10606' grown in a container.

The photograph at the top of the sheet is a close-up view of typical inflorescences of 'PER10606'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and the following observations and measurements describe plants grown in Encinitas, Calif. during the winter in a polyethylene-covered greenhouse and under conditions and practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Single plants were grown in 15.25-cm pots and pinched one time. Plants were three months old when the photographs and the detailed description were taken.

Botanical classification: *Euphorbia pulcherrima* 'PER10606'.

Parentage: Naturally-occurring whole plant mutation of the *Euphorbia pulcherrima* Willd. '7-05', not patented.

Propagation:

*Type.*—Terminal vegetative cuttings.

*Time to initiate roots.*—About five to seven days at 21° C.

*Time to produce a rooted young plant.*—About four weeks at 21° C.

*Root description.*—Fibrous; white in color.

Plant description:

*Plant habit and form.*—Uniform, upright and mounded plant habit; inverted triangle. Inflorescences positioned above the foliar plane. Moderately vigorous growth habit.

*Plant height.*—About 25 cm.

*Plant diameter or spread.*—About 43 cm.

*Lateral branch description.*—Quantity: Freely branching habit, about seven lateral branches develop after pinching. Length: About 22 cm. Diameter: About 5 mm. Internode length: About 2 cm. Strength: Strong. Texture: Smooth, glabrous. Color: Close to 146A.

*Foliage description.*—Arrangement: Alternate, simple. Length: About 11.5 cm. Width: About 7.8 cm. Shape: Ovate with occasional shallow lobes. Apex: Acuminate. Base: Obtuse. Margin: Entire; occasionally lobed. Venation pattern: Pinnate. Texture, upper surface: Smooth, glabrous. Texture, lower surface: Pubescence along venation. Surface: Rugose. Color: Developing foliage, upper surface: Close to 147A. Developing foliage, lower surface: Close to 147B. Fully developed, upper surface: Darker than 147A; venation, close to 146B. Fully expanded foliage, lower surface: Darker than 147B; venation, close to 147C. Petiole: Length: About 5 cm. Diameter: About 3 mm. Texture, upper and lower surfaces: Smooth, glabrous. Color, upper and lower surfaces: Close to 146C.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early season flowering; response time, plants flower about 8.5 weeks under natural season conditions in Encinitas, Calif.

*Post-production longevity.*—Excellent post-production longevity; plants of the new Poinsettia maintain good substance and bract color for about four weeks under interior conditions.

*Inflorescence size.*—Diameter: About 35 cm. Height (depth): About 7.5 cm to 8 cm.

*Flower bracts.*—Quantity per inflorescence: About 18. Length, largest bracts: About 14.1 cm. Width, largest bracts: About 11.6 cm. Shape: Ovate; occasionally with shallow lobes. Apex: Acuminate. Base: Obtuse. Margin: Entire; occasionally lobed. Texture, upper and lower surfaces: Smooth, glabrous. Aspect: About 30° from horizontal to nearly horizontal with development. Venation pattern: Pinnate. Color: Developing or transitional bracts, upper surface: Close to 150C. Developing or transitional bracts, lower surface: Close to 145B. Fully expanded bracts, upper surface: Close to 4D; venation, similar to lamina. Fully expanded bracts, lower surface: Close to 2D; venation, similar to lamina. Bract petiole: Length: About 2.8 cm. Diameter: About 2 mm. Texture, upper and lower surfaces: Smooth, glabrous. Color, upper and lower surfaces: Close to 145B to 145C.

*Cyathia.*—Quantity per corymb: About nine to ten. Diameter of cyathia cluster: About 2 cm by 2.5 cm. Length: About 8 mm. Width: About 5 mm. Shape: Ovoid. Color, immature: Close to 144A. Color, mature: Close to 144A to 144B. Nectaries: Quantity per cyathium: About one or two. Size: About 2 mm by 4 mm. Color: Close to 6A.

*Peduncles.*—Length: About 4 mm. Diameter: About 2 mm. Strength: Strong. Aspect: Mostly upright. Texture: Smooth, glabrous. Color: Close to 144B.

*Reproductive organs.*—Stamens: Quantity per cyathium: About five to six. Anther shape: Oval; bi-lobed. Anther length: Less than 1 mm. Anther color: Close to 7A. Amount of pollen: Scarce. Pollen color: Close to 7A. Pistils: Plants of the new Poinsettia do not develop pistils. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 30° C.

It is claimed:

1. A new and distinct Poinsettia plant named 'PER10606' as illustrated and described.

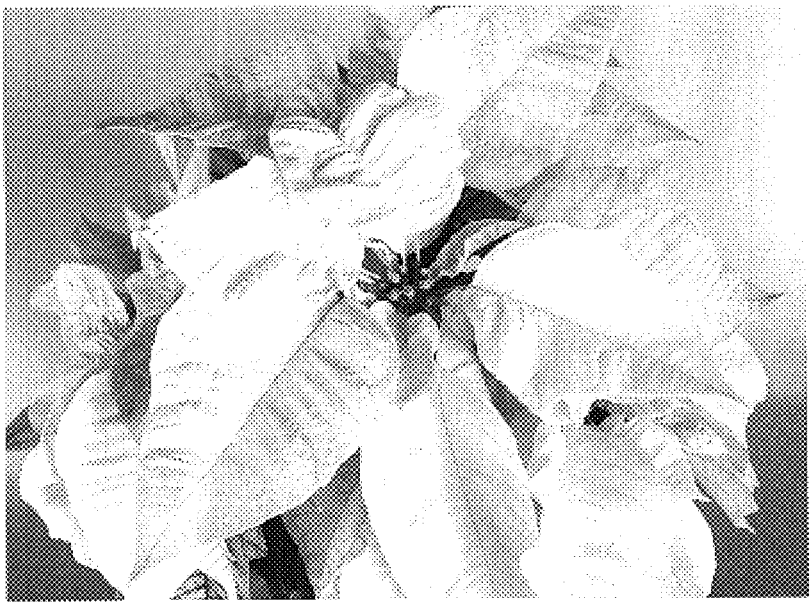
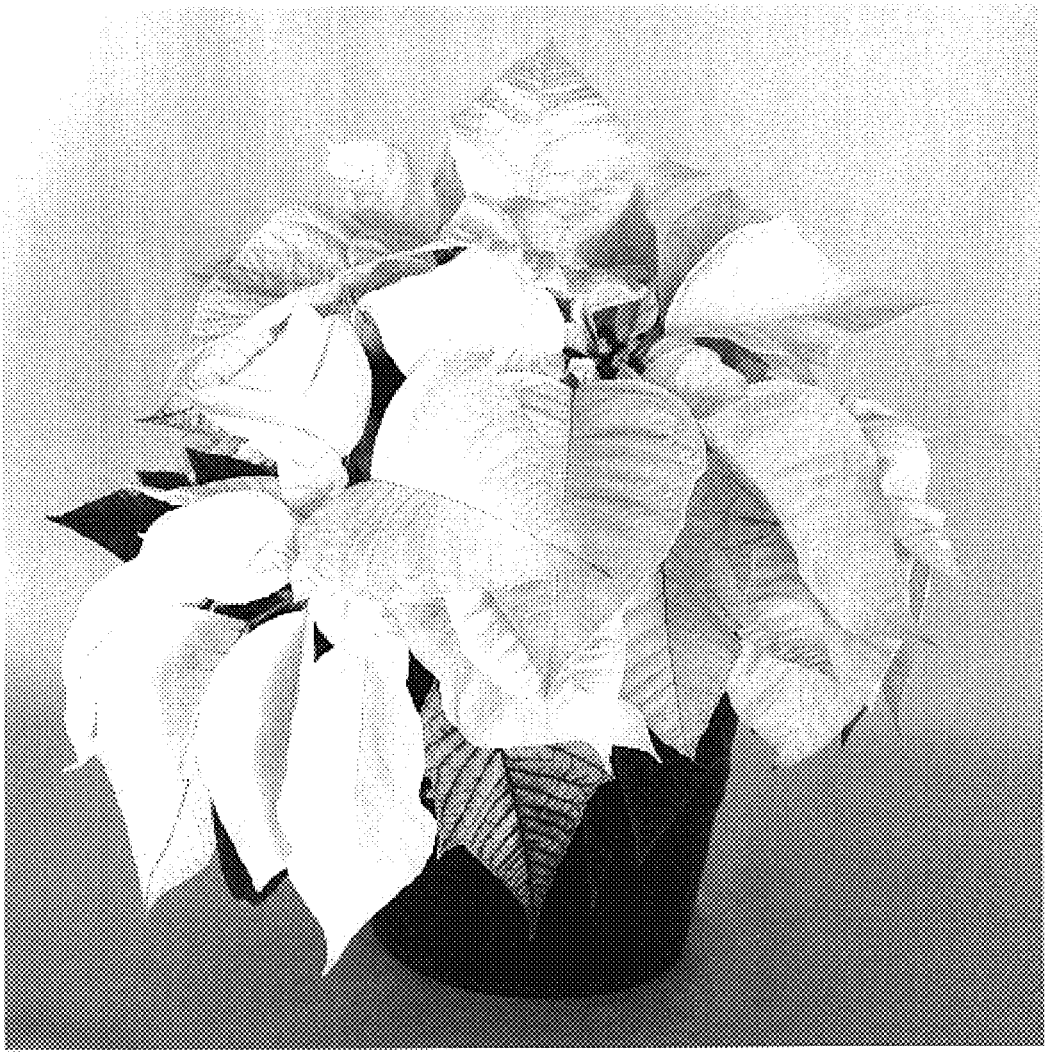

* * * * *